United States Patent
Shinde et al.

(10) Patent No.: US 10,314,871 B2
(45) Date of Patent: *Jun. 11, 2019

(54) ISOLATION OF OMEGA-7 FATTY ACID ETHYL ESTERS FROM NATURAL OILS

(71) Applicant: HELIAE DEVELOPMENT LLC, Gilbert, AZ (US)

(72) Inventors: Sandip Shinde, Gilbert, AZ (US); Stephen Ventre, Gilbert, AZ (US); Jennifer Lloyd-Randolfi, Chandler, AZ (US); Michael Lamont, Gilbert, AZ (US)

(73) Assignee: Heliae Development LLC, Gilbert, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/875,098

(22) Filed: Jan. 19, 2018

(65) Prior Publication Data

US 2018/0140650 A1 May 24, 2018

Related U.S. Application Data

(63) Continuation of application No. 15/157,047, filed on May 17, 2016, now Pat. No. 9,895,403, which is a continuation of application No. PCT/US2014/066699, filed on Nov. 20, 2014.

(60) Provisional application No. 61/907,437, filed on Nov. 22, 2013.

(51) Int. Cl.
| | |
|---|---|
| A61K 36/02 | (2006.01) |
| C12P 7/64 | (2006.01) |
| C11C 3/00 | (2006.01) |
| A61K 8/37 | (2006.01) |
| A61K 31/231 | (2006.01) |
| A61Q 19/00 | (2006.01) |

(52) U.S. Cl.
CPC ............... *A61K 36/02* (2013.01); *A61K 8/37* (2013.01); *A61K 31/231* (2013.01); *A61Q 19/00* (2013.01); *C11C 3/003* (2013.01); *C12P 7/6454* (2013.01)

(58) Field of Classification Search
CPC .............................. A61K 36/02; C11C 3/003
See application file for complete search history.

(56) References Cited

U.S. PATENT DOCUMENTS

| | | |
|---|---|---|
| 8,703,818 B2 | 4/2014 | Green |
| 9,200,236 B2 | 12/2015 | Shinde |
| 9,895,403 B2 * | 2/2018 | Shinde .................. A61K 36/02 |
| 2006/0088574 A1 | 4/2006 | Manning |
| 2009/0111876 A1 | 4/2009 | Hsieh |
| 2009/0221677 A1 | 9/2009 | Ntambi |
| 2012/0225941 A1 | 9/2012 | Green |
| 2013/0129775 A1 | 5/2013 | Shinde |

FOREIGN PATENT DOCUMENTS

| | | |
|---|---|---|
| EP | 2272383 | 1/2011 |
| WO | 2013075116 | 5/2013 |

OTHER PUBLICATIONS

Yang et al., "Chronic Administration of Palmitoleic Acid Reduces Insulin Resistance and Hepatic Lipid Accumulation in KK-Ay Mice with Genetic Type 2 Diabetes," Lipids in Health and Disease, 2011,10:120, 8 pages.
Alamu, et al "Effect of ethanol-palm kernel oil ratio on alkali-catalyzed biodiesel yield," Fuel 87 (2008) 1529-1533.
Bi, et al "Low-melting-point biodiesel derived from corn oil via urea complexation," Bioresource Technology 101 (2010) 1220-1226.
Braden, et al, "Dietary Polyunsaturated Fat in Relation to Mammary Carcinogenesis in Rats," Lipids, vol. 21, No. 4 (1986) 285-288.
Crexi, et al, Polyunsaturated Fatty Acid Concentrates on Carp Oil: Chemical Hydrolysis and Urea Complexation,: J Am Oil Chem Soc (2012) 89:329-334.
Curb, et al, "Serum Lipid Effectsof a High-Monounsaturated Fat Diet Based on Macadmia Nuts, " Arch Intern Med. 2000; 160: 1154-1158.
Wijendran, et al, "Dietary n-6 and n-3 Fatty Acid Balance and Cardiovascular Health," Annu. Rev. Nutr. 2004. 24:597-615.
Encinar et al., 'Biodiesel Fuels from Vegetable Oils: Transesterification of *Cynara cardunculus* L. Oils with Ethanol,' Energy & Fuels, 2002, 16, pp. 443-450.
Fjerbaek et al., "A Review of the Current State of Biodiesel Production Using Enzymatic Transesterification," Biotechnology and Bioengineering, Apr. 2009, vol. 102, No. 5, pp. 1298-1315.
Gogus, et al, n-Omega Fatty acids: a review of current knowledge,: International Journal of Food Science and Technology 2010, 45, 417-436.
Joseph, "Fatty Acid Composition of Comerical Menhaden, *Brevoortia* spp., Oil, 1982 and 1983." Marine Fisheries Review 47(3). 1985, 30-37.
Kaijser, et al, "Oxidative stability and lipid composition of macadamia nuts grown in New Zealand," Food Chemistry 71 (2000) 67-70.
Liu, etal, "Transesterification of soybean oil to biodiesel using CaO as a soild base catalyst," Fuel 87 (2008) 216-221.
Maedler, et al, "Distinct Effects of Saturated and Monounsaturated Fatty Acids on B-Cell Turnover and Function," Diabetes, vol. 50 (2001) 69-76.
Mata, et al, "Biodiesel Production from Corn Oil via Enzymatic Catalysis with Ethanol," Energy & Fuels 2012, 26, 3034-3041.

(Continued)

*Primary Examiner* — Golam M Shameem
(74) *Attorney, Agent, or Firm* — Veronica-Adele R. Cao; Heliae Development LLC

(57) ABSTRACT

Methods of producing high purity palmitoleic acid esters from natural oils are disclosed. The natural oils may comprise plant oil, nut oil, microalgae oil, and fish oil. The methods of processing the natural oil comprise transesterification with ethanol as the reacting solvent to produce ethyl esters. Methods of producing a high purity fraction of Omega-3, 6, & 9 fatty acid esters from natural oils are also disclosed. The high purity fatty acid esters may be used in nutrition, cosmetic, and nutraceutical products.

20 Claims, 8 Drawing Sheets

(56) References Cited

OTHER PUBLICATIONS

Media, et al."Concentration and Purification of Stearidonic, Eicosapentaenoic and Docosahexaenoic Acids from Cod Liver and the Marine Microalga Isochrysis galbana," JACS, vol. 72, No. 5 (1995) 575-583.

Modi et al, "Lipase-mediated conversion of vegetable oils into biodiesel using ethyl acetate as acyl acceptor," Bioresource Technology 98 (2007) 1260-1264.

Privett, et al, "Solubilities of Fatty Acids and Derivatives in Acetone," Hormel Institute Publication No. 159 (1956).

Rosi, et al, "Optimization of Molecular distillation to concentrate ethyl esters of eicosapentaenoic (20: 5 w-3) and docosahexaenoic acids (22: 6w-3) using simplified phenomenological modeling," J Sci Food Agric 2011; 91: 1452-1458.

Rubio-Rodriguez, et al, "Production of omega-3 polyunsaturated fatty acid concentrates: A review," Innovative Food and Science and Emerging Technologies 11 (2010) 1-12.

Ruxton, et al, "The impact of long-chain n-3 polyunsaturated fatty acids on human health." Nutriton Research Reviews (2005) 18, 113-129.

Schlenk, et al, "The Urea Complexes of Unsaturated Fatty Acids," Science, New Series, vol. 112, No. 2897 (Jul. 7, 1950), pp. 19-20.

Shahidi, et al, "Omega-3 fatty acid concentrates: nutritional aspects and production technologies", Trends in Food Science & Technology, 9(6), 230-240.

Simopoulos, "Evolutionary aspects of diet, the omega-6/omega-3 raio and genetic variation: nutritonal implications for chronic diseases," Biomedicine & Pharmaotherapy 60 (2006) 502-507.

Simopoulos, "The imprtance of the ratio of omega-6/omega-3 essential fatty acids," Biomed Pharmacother 56 (2002) 365-379.

Tempe, "Dietary fats and coronary heart disease," Biomed & Pharmacother 1996; 50: 261-268.

Wansadundra, et al "Concentration of omega-3 polyunsaturated fatty acids of seal blubber oil by urea complexation: optimization of reaction conditions," Food Chemistry 65 (1999) 41-49.

Zabeti et al., 'Activity of Solid Catalysts for Biodiesel Production: A Review,' Fuel Processing Technology, 90, 2009, pp. 770-777.

* cited by examiner

ISOLATION OF OMEGA-7 FATTY ACID ETHYL ESTERS FROM NATURAL OILS

CROSS REFERENCE TO RELATED APPLICATIONS

This application claims the benefit of U.S. Provisional Application No. 61/907,437, filed Nov. 22, 2013, entitled Isolation of Omega-7 Fatty Acids From Natural Sources of Oil in Ethyl Ester Form, PCT Application No. PCT/US2014/066699, filed Nov. 20, 2014, entitled Isolation of Omega-7 Fatty Acid Ethyl Esters from Natural Oils, and U.S. application Ser. No. 15/157,047, filed May 17, 2016, entitled Isolation of Omega-7 Fatty Acid Ethyl Esters from Natural Oils, the entire contents of which are hereby incorporated by reference herein.

BACKGROUND

Long chain polyunsaturated fatty acids (PUFA's) [e.g., C18-C22 (Omega-3 and 6)] are generally found in plants and marine sources, and are widely accepted in commercial cosmetic and health applications due to their beneficial effects on metabolism. The most common essential fatty acids are linoleic acid (LA) [C18:2n6, Omega-6] and α-linolenic acid (α-LN) [C18:3n3, Omega-3], and are responsible for the production of prostaglandins (PG) that control blood vessels and other body functions. Eicosapentaenoic acid (EPA) [C20:5n3, Omega-3] and docosahexaenoic acid (DHA) [C22:6n3, Omega-3] may be formed through the conversion of dietary linolenic acid, and are known to be essential for health and nutrition, resulting in an increase in commercial interest in recent years. EPA and DHA, are known to be potent antiarryhthmic agents and also improve vascular endothelial function, help lower blood pressure, platelet sensitivity, and the serum triglyceride level. In 2005 Simpson et. al (The impact of long-chain n-3 polyunsaturated fatty acids on human health. *Nutrition research reviews* (2005), 18, pp. 113-29) concluded that there is strong evidence of the clinical benefit of this type of Omega-3 PUFA on cardiovascular diseases or rheumatoid arthritis. Palmitoleic acid (C16:1n7, Omega-7) has also recently begun to receive an increase in commercial interest and has shown beneficial effects on cholesterol, low-density lipoprotein cholesterol levels, and also on reducing muscle insulin resistance and preventing beta-cell apoptosis.

As shown in Tables 1 and 2, trans fatty acids, cholesterol, and saturated fats responsible for atherosclerosis are fairly common in vegetable oil, fish oil, and marine products. Additionally, Omega-3 PUFA's are beneficial in reducing cholesterol and the risk of myocardial infarction. Hypertriglyceridaemia, which causes an increase in serum triglyceride in blood level, can cause cardiovascular diseases that may be prevented by replacing saturated fats with Omega-3 PUFAs. Synthesis and subsequent purification of essential fatty acid ethyl esters provides an opportunity to separate unwanted saturated fat from essential fatty acids.

TABLE 1

Fat content/EPA + DHA (g 100 g$^{-1}$) ratio of some various fish, marine products, vegetables and oils

| | Fat content (g 100 g$^{-1}$) | EPA + DHA (g 100 g$^{-1}$) | Fat content/(EPA + DHA) (g 100 g$^{-1}$) ratio |
|---|---|---|---|
| Eel | 24.5 | 0.83 | 29.51 |
| Hering | 17.8 | 2.72 | 6.54 |
| Sprat | 16.6 | 3.23 | 5.14 |
| Tuna | 15.5 | 3.37 | 4.60 |
| Salmon | 13.6 | 2.86 | 4.76 |
| Mackerel | 11.9 | 1.75 | 6.8 |
| Carp | 4.8 | 0.30 | 16 |
| Sardine | 4.5 | 1.39 | 3.24 |
| Swordfish | 4.4 | 1.79 | 2.45 |
| Trout | 2.7 | 0.59 | 4.58 |
| Halibut | 1.7 | 0.51 | 3.33 |
| Cod | 0.6 | 0.18 | 3.33 |
| Haddock | 0.6 | 0.16 | 3.75 |
| Lobster | 1.9 | 0.20 | 9.5 |
| Shrimp | 1.4 | 0.30 | 4.66 |
| Mussels | 1.4 | 0.15 | 9.33 |
| Anchovy | 2.3 | 0.50 | 4.60 |
| Sardine | 13.9 | 2.44 | 5.70 |

TABLE 2

| | Fat content (g 100 g$^{-1}$) | α-LN (g 100 g$^{-1}$) | Fat content/α-LN (g 100 g$^{-1}$) ratio |
|---|---|---|---|
| Butter | 83.2 | 1.20 | 69.3 |
| Lard | 100.0 | 0.98 | 102.04 |
| Linseed oil | 100.0 | 54.2 | 1.84 |
| Soybean oil | 100.0 | 7.70 | 12.98 |
| Rapeseed oil | 100.0 | 9.15 | 10.93 |
| Walnut oil | 100.0 | 13.5 | 7.40 |
| Olive oil | 100.0 | 0.86 | 625 |
| Vegetable oil | 80.0 | 2.40 | 33.3 |
| Almonds | 54.1 | 0.26 | 208.07 |
| Hazelnut | 61.6 | 0.15 | 410.6 |
| Walnuts | 62.5 | 6.80 | 9.19 |
| Kale | 0.90 | 0.35 | 2.57 |
| Lettuce | 0.22 | 0.07 | 3.14 |
| Parsley | 0.36 | 0.12 | 3.00 |
| Potato | 0.11 | 0.02 | 5.5 |
| Cauliflower | 0.18 | 0.10 | 1.8 |
| Spinach | 0.30 | 0.13 | 2.31 |
| White cabbage | 0.20 | 0.09 | 2.22 |
| Wheat bran | 4.65 | 0.16 | 29.06 |

While sources and applications of Omega-3s have been developed commercially, the use of purified fatty acids in nutrition applications may extend beyond Omega-3s. Purified Omega-6, 7 & 9's may also be used in nutrition, cosmetic, and nutraceutical application to provide a more complete health or personal care product. Yang et. al (Chronic administration of palmitoleic acid reduces insulin resistance and hepatic lipid accumulation in KK-Ay Mice with genetic type 2 diabetes. *Lipids in health and disease* 10, 120 (2011)) showed that oral administration of palmitoleic acid (Omega-7) to KK-Ay mice dramatically improved their diabetic condition. Also, hyperglycemia and hypertriglyceridemia were reduced in the mice with the oral administration of palmitoleic acid, while palmitic acid (saturated fat) was completely ineffective in providing the same effects. Maedler et. al (Distinct Effects of Saturated and Monosaturated Fatty Acids on Beta-Cell Turnover and Function. *Diabetes* (January 2001), vol. 50, no. 1, pp. 69-76) showed the harmful effect of palmitate on β-cell turnover while in contrast, the monounsaturated palmitoleic acid does not affect β-cell apoptosis but instead promotes β-cell proliferation. In promoting β-cell proliferation, palmitoleic acid counteracted the negative effects of palmitate (an anion of palmitic acid) as well as improved β-cell function. Therefore purifying Omega-7 rich oil by removing saturated fat may provide Omega-7s in a beneficial form suited for nutrition applications. Such purified Omega-7 fractions may be produced by synthesis of ethyl esters and their purification.

In addition to purified Omega-7s, purified Omega-6s also have an important role in the commercial nutrition market. The ratio of essential fatty acids is crucial to nutrition, as western diets are generally deficient in Omega-3 fatty acids and have excessive amounts of Omega-6 fatty acids. According to Simopoulos et. al (Evolutionary aspects of diet, the omega-6/omega-3 ratio and genetic variation: nutritional implications for chronic diseases. *Biomedicine & pharmacotherapy* (2006), 60, pp. 502-507; The importance of the ratio of omega-6/omega-3 essential fatty acids. *Biomedicine & pharmacotherapy* (2002), 56, pp. 365-379), a lower ratio of Omega-6/Omega-3 fatty acids is desirable for reducing the risk of many chronic diseases. Synthesis of ethyl esters and their subsequent purification provides the opportunity for formulation of nutritionally relevant ratios of essential fatty acids like Omega-3 and Omega-6. Therefore, there is a need in the art for methods of producing high purity esters of Omega 3, 6, 7, & 9 fatty acids for use in nutrition, cosmetic, and nutraceutical products.

SUMMARY

Disclosed are methods for isolating high purity fractions of Omega-3, 6, 7, & 9 ethyl esters. The high purity isolated fatty acid ester fractions may be used in nutrition, cosmetic, and nutraceutical products.

In one embodiment of the invention, a method of producing high purity palmitoleic acid ethyl esters comprises: providing an oil; transesterifying the oil with a catalyst and ethanol as a reacting solvent to produce ethyl esters; distilling the ethyl esters to produce a first fraction comprising C18:1n9 ethyl esters and a second fraction comprising C16:0 and C16:1n7 ethyl esters; and separating the C16:0 and C16:1n7 ethyl esters of the second fraction to produce a third fraction of C16:0 ethyl esters and a fourth fraction comprising at least 50% w/w C16:1n7 ethyl esters. In some embodiments, the oil may consist of a natural oil comprising at least 5% C16:1n7 fatty acid. In some embodiments, the natural oil may comprise at least one oil selected from the group consisting of macadamia nut oil, menhaden oil, and anchovy oil.

In some embodiments, the catalyst of the transesterifying step may comprise at least one catalyst selected from the group consisting of: NaOH, KOH, sodium ethoxide, HCl, $BF_3$, $H_3PO_4$, an organic sulfonic acid, sulphuric acid, a metal oxide, Mg—Al hydrolalcite, and an immobilized enzyme. In some embodiments, the molar ratio of ethanol in the transesterifying step may be in the range of 1:3 to 1:15, and preferably in the range of 1:9 to 1:11. In some embodiments, the transesterifying step may have a yield of 70-90%.

In some embodiments, the distillation step may comprise at least one selected from the group consisting of one pass vacuum distillation, two pass vacuum distillation, fractional distillation, and simple molecular distillation. In some embodiments, the separation step may comprise at least one selected from the group consisting of urea complexation, crystallization, filtration, extraction, and adsorption chromatography. In some embodiments, the separated C16:1n7 esters fraction may comprise 50-90% w/w C16:1n7 ethyl esters.

In another embodiment of the invention, a method of producing high purity palmitoleic acid ethyl esters comprises: providing a microalgae oil; transesterifying the microalgae oil with a catalyst and ethanol as a reacting solvent in a reaction comprising at least one stage to produce ethyl esters; distilling the ethyl esters to produce a first fraction comprising C18:1n9, C20:4n6, and C20:5n3 ethyl esters, and a second fraction comprising C16:0 and C16:1n7 ethyl esters; and separating the C16:0 and C16:1n7 ethyl esters of the second fraction to produce a third fraction of C16:0 ethyl esters and a fourth fraction comprising at least 35% w/w C16:1n7 ethyl esters. In some embodiments, the microalgae oil may consist of a natural microalgae oil comprising at least 5% C16:1n7 fatty acid. In some embodiments, the natural microalgae oil may comprise oil derived from at least one microalga from a genus selected from the group consisting of *Nannochloropsis, Nitzschia, Thalasossira,* and *Phaeodactylum.*

In some embodiments, the molar ratio of ethanol in the transesterifying step may be in the range of 1:3 to 1:15, and preferably in the range of 1:6 to 1:8. In some embodiments, the transesterifying step may comprise two stages of transesterification reactions. In some embodiments, the two stages of transesterification reactions may use different catalysts. In some embodiments, the transesterifying step may have a yield of 60-80%. In some embodiments, the transesterifying step may be performed at 75-85° C. In some embodiments, the separated C16:1n7 esters fraction may comprise 35-50% w/w C16:1n7 ethyl esters.

In another embodiment of the invention, a composition comprises a mixture of esters derived an oil comprising at least 5% C16:1n7 fatty acid, wherein the mixture of esters comprises at least 50% w/w C16:1n7 ethyl esters. In some embodiments, the oil may comprise at least one natural oil selected from the group consisting of macadamia nut oil, menhaden oil, and anchovy oil. In some embodiments, the mixture of esters derived from natural macadamia nut oil comprises 50-90% w/w C16:1n7 ethyl esters. In some embodiments, the mixture of esters derived from natural macadamia nut oil further comprises 10% or less C16:0 ethyl esters. In some embodiments, the mixture of esters derived from natural macadamia nut oil further comprises 5-10% C16:0 ethyl esters. In some embodiments, the mixture of esters derived from macadamia nut oil further comprises 5% or less C18:1n9 ethyl esters. In some embodiments, the mixture of esters derived from natural macadamia nut oil further comprises 0.5-5% C18:1n9 ethyl esters.

In another embodiment of the invention, a composition comprises a mixture of esters derived from microalgae oil comprising at least 5% C16:1n7 fatty acid, wherein the mixture of esters comprises at least 30% w/w C16:1n7 ethyl esters. In some embodiments, the microalgae oil may comprise a natural oil derived from at least one microalga from a genus selected from the group consisting of *Nannochloropsis, Nitzschia, Thalasossira,* and *Phaeodactylum.* In some embodiments, the mixture of esters derived from natural *Nannochloropsis* oil comprises 30-50% w/w C16:1n7 ethyl esters. In some embodiments, the mixture of esters derived from natural *Nannochloropsis* oil further comprises 50% or less C16:0 esters. In some embodiments, the mixture of esters derived from natural *Nannochloropsis* oil further comprises 5-50% C16:0 ethyl esters. In some embodiments, the mixture of esters derived from *Nannochloropsis* oil further comprises 10% or less C18:1n9 ethyl esters. In some embodiments, the mixture of esters derived from natural *Nannochloropsis* oil further comprises 0.5-10% C18:1n9 ethyl esters.

BRIEF DESCRIPTION OF THE FIGURES

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION

Figure 1:
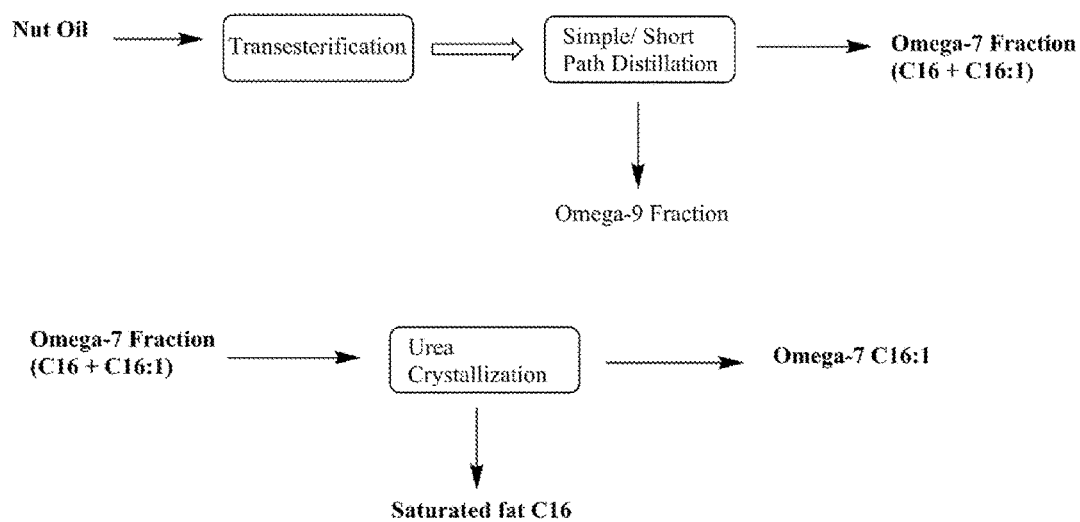
FIG. 1 illustrates one non-limiting embodiment for isolating an Omega-7 product from natural nut oil.

A number of nutrition, cosmetic, and nutraceutical products may be produced from oils comprising Omega-3, 6, 7 & 9 fatty acids. In some embodiments, the oil may comprise a natural oil comprising plant oil, nut oil, microalgae oil, or fish oil derived from plants or animals that have not been genetically or transgenically modified, and has not been previously purified to remove certain constituents (e.g., targeted fatty acids). In some embodiments, the oil may be derived from plant oil, nut oil, microalgae oil, or fish oil derived from plants or animals that have been genetically or transgenically modified, may be previously purified to remove certain constituents (e.g., targeted fatty acids), may be synthesized, or combinations thereof. In some embodiments, the oil may comprise at least 5% C16:1n7 fatty acid. In some embodiments, the oil may comprise 5-30% C16:1n7 fatty acid. In some embodiments, the oil may comprise 5-25% C16:1n7 fatty acid. In some embodiments, the oil may comprise 5-10% C16:1n7 fatty acid. In some embodiments, the oil may comprise 10-20% C16:1n7 fatty acid. In some embodiments, the oil may comprise 20-30% C16:1n7 fatty acid. In some embodiments, the oil may be high in C16:1n7 fatty acid (Omega-7) and comprise plant oil (e.g., sea buckthorn), nut oil (e.g., macadamia), microalgae oil (e.g., *Nannochloropsis, Nitzschia, Thalasossira, Phaeodactylum*), or fish oil (e.g., menhaden, anchovy). In some embodiments, the oil may be processed in a multiple step process to produce high purity Omega-3, 6, 7 and/or 9 oil products. The targeted end product may influence the method steps and inputs in the oil processing methods.

In some embodiments, processing of the oil may comprise at least one transesterification step. In some embodiments, processing of the oil may comprise a distillation step comprising at least one distillation method selected from the group consisting of simple molecular distillation, short path distillation, one pass vacuum distillation, two pass vacuum distillation, and fractional distillation. In some embodiments, processing of the oil may comprise a separation step comprising at least one separation method selected from the group consisting of urea complexation, crystallization, filtration, extraction, and adsorption chromatography. In some embodiments, processing of the oil may comprise combinations of the steps described throughout the specification.

Using the methods and 1 oils described throughout the specification, the inventors surprisingly found that purity levels of Omega-7 esters could be attained that were not previously achievable, particularly purity levels of Omega-7 esters could be attained from natural oils. In some embodiments, processing of the oil may result in a high purity Omega-7 product with a concentration of palmitoleic acid (C16:1n7) esters of at least 30% w/w. In some embodiments, processing of the oil may result in a high purity Omega-7 product with a concentration of palmitoleic acid (C16:1n7) esters of at least 50% w/w. In some embodiments, processing of the oil may result in a high purity Omega-7 product with a concentration of palmitoleic acid (C16:1n7) esters of at least 70% w/w. In some embodiments, processing of the oil may result in a high purity Omega-7 product with a concentration of palmitoleic acid (C16:1n7) esters of at least 80% w/w. In some embodiments, processing of the oil may result in a high purity Omega-7 product with a concentration of palmitoleic acid (C16:1n7) esters of 30-90% w/w. In some embodiments, processing of the oil may result in a high purity Omega-7 product with a concentration of palmitoleic acid (C16:1n7) esters of 30-50% w/w. In some embodiments, processing of the oil may result in a high purity Omega-7 product with a concentration of palmitoleic acid (C16:1n7) esters of 50-70% w/w. In some embodiments, processing of the oil may result in a high purity Omega-7 product with a concentration of palmitoleic acid (C16:1n7) esters of 70-90% w/w.

In some embodiments, processing of the oil may result in an Omega-7 & 9 product with a combined concentration of C16:1n7 and C18:1n9 esters of at least 40% w/w. In some embodiments, processing of the oil may result in an Omega-7 & 9 product with a combined concentration of C16:1n7 and C18:1n9 esters of at least 50% w/w. In some embodiments, processing of the oil may result in an Omega-7 & 9 product with a combined concentration of C16:1n7 and C18:1n9 esters of at least 70% w/w. In some embodiments, processing of the oil may result in an Omega-7 & 9 product with a combined concentration of C16:1n7 and C18:1n9 esters of at least 80% w/w. In some embodiments, processing of the oil may result in an Omega-7 & 9 product with a combined concentration of C16:1n7 and C18:1n9 esters of 30-90% w/w. In some embodiments, processing of the oil may result in an Omega-7 & 9 product with a combined concentration of C16:1n7 and C18:1n9 esters of 30-50% w/w. In some embodiments, processing of the oil may result in an Omega-7 & 9 product with a combined concentration of C16:1n7 and C18:1n9 esters of 50-70% w/w. In some embodiments, processing of the oil may result in an Omega-7 & 9 product with a combined concentration of C16:1n7 and C18:1n9 esters of 70-90% w/w.

In some embodiments, processing of the oil may result in a concentration of C16:0 esters of less than 50% w/w. In some embodiments, processing of the oil may result in a concentration of C16:0 esters of less than 40% w/w. In some embodiments, processing of the oil may result in a concentration of C16:0 esters of less than 30% w/w. In some embodiments, processing of the oil may result in a concentration of C16:0 esters of less than 20% w/w. In some embodiments, processing of the oil may result in a concentration of C16:0 esters of less than 10% w/w. In some embodiments, processing of the oil may result in a concentration of C16:0 esters ranging from 5-50% w/w. In some embodiments, processing of the oil may result in a concentration of C16:0 esters ranging from 5-40% w/w. In some embodiments, processing of the oil may result in a concentration of C16:0 esters ranging from 5-30% w/w. In some embodiments, processing of the oil may result in a concentration of C16:0 esters ranging from 5-20% w/w. In some embodiments, processing of the oil may result in a concentration of C16:0 esters ranging from 5-10% w/w.

In some embodiments, processing of the oil may result in a concentration of C18:1n9 esters of less than 30% w/w. In some embodiments, processing of the oil may result in a concentration of C18:1n9 esters of less than 20% w/w. In some embodiments, processing of the oil may result in a concentration of C18:1n9 esters of less than 10% w/w. In some embodiments, processing of the oil may result in a concentration of C18:1n9 esters of less than 5% w/w. In some embodiments, processing of the oil may result in a concentration of C18:1n9 esters of less than 1% w/w. In some embodiments, processing of the oil may result in a concentration of C18:1n9 esters ranging from 0.5-30% w/w. In some embodiments, processing of the oil may result in a concentration of C18:1n9 esters ranging from 0.5-20% w/w. In some embodiments, processing of the oil may result in a concentration of C18:1n9 esters ranging from 0.5-10% w/w. In some embodiments, processing of the oil may result in a concentration of C18:1n9 esters ranging from 0.5-5% w/w. In some embodiments, processing of the oil may result in a concentration of C18:1n9 esters ranging from 0.5-1% w/w.

Transesterification

Synthesis of ethyl esters is known in the art for the enrichment of Omega-3 fatty acids, and the inventors found that such synthesis may also be adapted for application to Omega-6, 7 & 9 fatty acids. Transesterification of Omega-7 rich oil may be performed using a variety of different catalysts and conditions. In some embodiments, the transesterification may be performed enzymatically, with an acid or base catalyst, a heterogeneous catalyst, or combinations thereof. In some embodiments, the base catalyst may comprise NaOH, KOH, sodium ethoxide, and combinations thereof. In some embodiments, the acid catalyst may comprise HCl, $BF_3$, $H_3PO_4$, organic sulfonic acids, and combinations thereof. In some embodiments, the heterogeneous catalyst may comprise metal oxide (e.g., CaO, MgO, SrO, ZnO, $La_2O_3$), Mg—Al hydrolalcite, and combinations thereof. In some embodiments, the enzymatic method may comprise immobilized enzyme-based catalysts, such as those commercially available from TransBiodiesel Ltd. (P.O. Box 437, Shfar-Am 20200 Israel).

In some embodiments, the catalyst may preferably comprise at least one catalyst selected from the group consisting of sulphuric acid and sodium ethoxide. In some embodiments, the transesterification method may use methanol as a reacting solvent and produce fatty acid methyl esters (FAMEs). In some embodiments, the transesterification method may use ethanol as a reacting solvent and produce fatty acid ethyl esters (FAEEs). In some embodiments, the molar ratio of the reacting solvent may range from 1:3 to 1:15. In some embodiments, the molar ratio of the reacting solvent may range from 1:4 to 1:14. In some embodiments, the molar ratio of the reacting solvent may range from 1:5 to 1:13. In some embodiments, the molar ratio of the reacting solvent may range from 1:5 to 1:12. In some embodiments, the molar ratio of the reacting solvent may range from 1:7 to 1:10. In some embodiments, the molar ratio of the reacting solvent may range from 1:6 to 1:8. In some embodiments, the molar ratio of the reacting solvent may range from 1:9 to 1:11.

In some embodiments, the temperature of the transesterification step may comprise a temperature in the range of 70-90° C. In some embodiments, the temperature of the transesterification step may comprise a temperature in the range of 75-85° C. In some embodiments, the temperature of the transesterification step may comprise a temperature in the range of 76-84° C. In some embodiments, the temperature of the transesterification step may comprise a temperature in the range of 77-83° C. In some embodiments, the temperature of the transesterification step may comprise a temperature in the range of 78-82° C. In some embodiments, the temperature of the transesterification step may comprise a temperature in the range of 79-81° C.

In some embodiments, the yield of the transesterification step may comprise at least 50%. In some embodiments, the yield of the transesterification step may comprise 50-90%. In some embodiments, the yield of the transesterification step may comprise 60-80%. In some embodiments, the yield of the transesterification step may comprise 70-90%. In some embodiments, the yield of the transesterification step may comprise 75-90%. In some embodiments, the yield of the transesterification step may comprise 80-90%. In some embodiments, the yield of the transesterification step may comprise 75-85%.

Purification of Esters

Purification of esters may be performed with adsorption chromatography, fractional or simple molecular distillation, low-temperature crystallization (winterization), supercritical fluid extraction, solvent extraction, and urea complexation. Suitable solvents for extraction include, but are not limited to ethanol, methanol, and hexane. With the help of proper absorbents, adsorption chromatography may be used to separate the esters based on the number of carbons as well as the degree of unsaturation. In some embodiments, such absorbents may comprise $AgBF_4$/SBA15.HPSiOEtIM.$PF_6$, Silver resin Chromatography, Ag+ immobilized by ionic liquid precursor molecules covalently bonded to silica gel, and mesoporous SBA-15.

Molecular distillation is known in the art to be useful for the separation, purification and concentration of thermolabile substances with low vapor pressure. Molecular distillation techniques may be used as simple or short path distillation, especially when purifying crude esters such as but not limited to microalgae oil FAEEs. Fractional distillation also provides a method of producing higher purity FAEEs from oils, such as but not limited to nut oil FAEE (e.g., macadamia) or fish oil FAEE (e.g., menhaden, anchovy).

In some embodiments, the distillation may comprise one pass or multiple pass vacuum distillation and take place under pressure. In some embodiments, the distillation may take place under pressure ranging from 0.1-10 mm Hg. In some embodiments, the distillation may take place under pressure ranging from 0.2-7.5 mm Hg. In some embodiments, the distillation may take place under pressure ranging from 0.3-5 mm Hg. In some embodiments, the distillation may take place under pressure ranging from 1-4 mm Hg. In some embodiments, the distillation may take place under pressure ranging from 2-3 mm Hg. In some embodiments, multiple passes in a distillation take place at the same pressures. In some embodiments, multiple passes in a distillation take place at different pressures In some embodiments, the temperature during distillation may range from 140-280° C. In some embodiments, the temperature during distillation may range from 160-270° C. In some embodiments, the temperature during distillation may range from 170-250° C. In some embodiments, the temperature during distillation may range from 180-225° C. In some embodiments, the temperature during distillation may range from 190-210° C. In some embodiments, the distillation may comprise a single pass at a constant temperature. In some embodiments, the distillation may comprise a single pass at varying temperatures. In some embodiments, the distillation may comprise multiple passes at the same temperature. In some embodiments, the distillation may comprise multiple passes at different temperatures.

Low-temperature crystallization (winterization) may also be used to produce high purity esters, and takes advantage of the solubility of the esters in different solvents. In some embodiments, the solvents may comprise: alcohols (e.g., methanol, ethanol), esters (e.g., ethyl acetate), ethers (e.g., diethyl ether), ketones (e.g., acetone), aromatic hydrocarbons (e.g., toluene), hydrocarbons (e.g., hexane), and n-heptane. In some embodiments, low-temperature crystallization may be used to purify the Omega-3 EPA or DHA fatty acids or esters from oil with higher concentrations of EPA or DHA, such as fish or microalgae oil. Urea complexation may also be used to effectively separate the saturated fat from PUFAs. In some embodiments, urea complexation may be used with simple principle straight-chain saturated fatty acids with six carbon atoms confined in the complex. In such six carbon atom embodiments, the presence of double bonds in the fatty acids increases the bulk of the molecule and reduces the likelihood of the molecule's complexation with urea, which helps to achieve the separation.

In some embodiments, the temperature of the urea complexation step may comprise a temperature in the range of 70-90° C. In some embodiments, the temperature of the urea complexation step may comprise a temperature in the range of 75-85° C. In some embodiments, the temperature of the urea complexation step may comprise a temperature in the range of 76-84° C. In some embodiments, the temperature of the urea complexation step may comprise a temperature in the range of 77-83° C. In some embodiments, the temperature of the urea complexation step may comprise a temperature in the range of 78-82° C. In some embodiments, the temperature of the urea complexation step may comprise a temperature in the range of 79-81° C.

Example 1

An experiment was conducted to determine the purity of Omega-7 ethyl esters that could be isolated from natural macadamia nut oil. Natural macadamia nut oil was analyzed and found to contain the fatty acid profile as shown in Table 3.

TABLE 3

| Natural Macadamia Oil Composition | |
|---|---|
| Analyte | % |
| C14:0 | 1.1 |
| C16:0 | 8.3 |
| C16:1n7 (Omega-7) | 22.0 |
| C18:0 | 3.1 |
| C18:1n9 (Omega-9) | 53.7 |

TABLE 3-continued

| Natural Macadamia Oil Composition | |
|---|---|
| Analyte | % |
| C18:1n11t | 4.2 |
| C18:2 | 2.3 |
| C20:0 | 2.8 |
| C20:1 | 2.6 |
| Total Fatty Acids | 100.0 |

One non-limiting embodiment of the multi-step process for producing an isolated high purity Omega-7 product from natural nut oil, such as macadamia nut oil, is shown in FIG. 1.

Transesterification Step:

Macadamia nut oil (1 kg) was transesterified in a 5 L, 3-neck round bottom flask using 2.5% w/w sodium ethoxide as the catalyst and 1:10 molar ratio of ethanol as the reacting solvent to produce an FAEE product. The reaction was performed for 3 hrs at 80° C. After 3 hrs, the reaction mixture was cooled to ≤40° C. and neutralized with 1:1 v/v of water. After neutralization the reaction mixture was allowed to separate into two layers comprising an ethyl ester layer on top and an aqueous layer on bottom. The ethyl ester layer was separated and was concentrated using a rotary evaporator resulting in ≥850 grams of the FAEE product (≥85% Yield).

Distillation Step:

For macadamia nut oil FAEE with a composition of at least 20% w/w C16:1n7 (palmitoleic acid) and using a vacuum distillation apparatus in either a one-pass or two-pass system, it is possible to produce an oil product with a concentration of C16:1n7 ethyl esters above 50% w/w. In such a system, the reboiler temperature varied between 170° C. and 220° C., and the vacuum pressure was maintained at 0.3 to 5 mm Hg. Using a single pass vacuum distillation system with the macadamia nut oil FAEE product from the transesterification step resulted in a concentrated oil product mixture of C16:0 and C16:1n7 ethyl esters (second fraction) as shown in Table 4. The resulting second fraction concentrated oil product may be successfully used in the cosmetics field, as the saturated fat along with Omega-7 also has antimicrobial activity. A significant portion of Omega-9 ethyl esters (C18:1n9) were separated from the Omega-7 ethyl esters in the molecular distillation step to form a first fraction, and the first fraction comprising Omega-9 ethyl esters may be used in nutrition products for heart health, blood sugar control, managing cholesterol levels, and promoting healthy inflammation responses.

TABLE 4

| Single pass distillate | |
|---|---|
| Analyte | % |
| C12:0 | 1.1 |
| C14:0 | 5.9 |
| C16:0 | 19.0 |
| C16:1n7 (Omega-7) | 73.4 |
| C18:0 | 0.0 |
| C18:1n9 (Omega-9) | 0.8 |
| Total Fatty Acid Esters | 100.1 |

Separation Step:

The second fraction concentrated oil product (20 grams) resulting from the molecular distillation step was treated with urea (2 times w/w) and ethanol (5 times w/v). The resulting reaction mixture was refluxed at 80° C. for 2 hrs and then allowed to crystallize overnight (approximately 10-12 hrs). After overnight crystallization, the resulting crystals comprising saturated fats (C16:0) were separated from the liquid phase using a simple filtration system to form a third fraction of C16:0 ethyl esters. The liquid phase filtrate (fourth fraction) was treated with water to remove the dissolved urea and the Omega-7 ethyl ester product was extracted using hexane. The hexane layer was then concentrated using a rotary evaporator under vacuum to give the product composition as shown in Table 5.

TABLE 5

Urea crystallization

| Analyte | % |
|---|---|
| C12:0 | 0.61 |
| C14:0 | 3.17 |
| C16:0 | 7.44 |
| C16:1n7 (Omega-7) | 86.37 |
| C18:1n9 (Omega-9) | 1.43 |
| Total Fatty Acid Esters | 99.02 |

Figure 2:
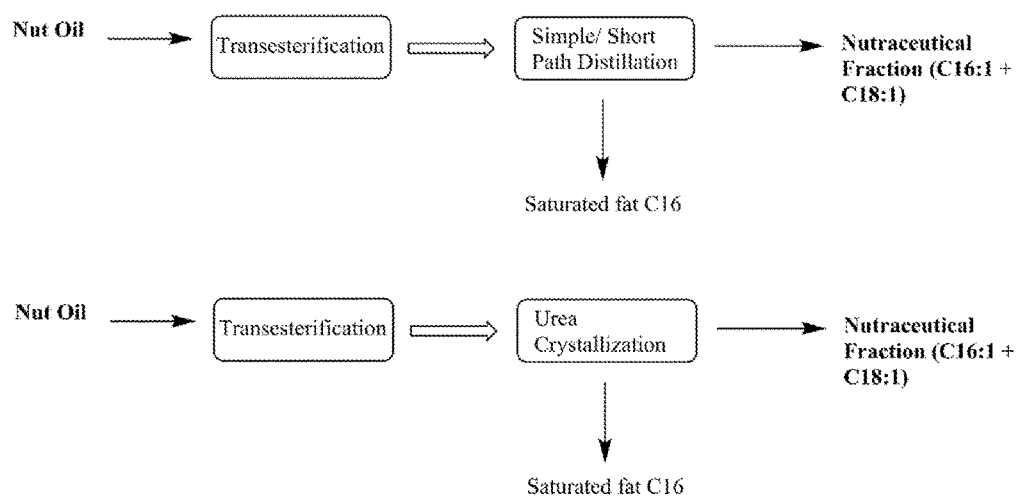
FIG. 2 illustrates a non-limiting embodiment for isolating an Omega-7 & 9 product from natural nut oil.

Additionally, a nutraceutical fraction comprising C16:1n7 and C18:1n9 ethyl esters may be obtained from macadamia nut oil FAEE by using either a molecular distillation method to remove fatty acids≤C16:0 or by using a urea complexation method to remove saturated fat after transesterification, as shown in FIG. 2.

Example 2

An experiment was conducted to determine the purity of Omega-7 ethyl esters that could be isolated from natural microalgae oil. Microalgae from genera such as *Nannochloropsis, Nitzschia, Thalasossira*, and *Phaeodactylum* are known to be sources of Omega-7 as well as sources of Omega-3 (EPA, DHA) fatty acids. Similar to the macadamia nut oil in Example 1, the oil derived from *Nannochloropsis* may also be processed to produce a high purity Omega-7 product. Natural *Nannochloropsis* oil was analyzed and found to contain the fatty acid profile shown in Table 6.

TABLE 6

Natural Nannochloropsis Oil

| Analyte | % |
|---|---|
| C14:0 Myristic | 4.0 |
| C16:0 Palmitic | 32.1 |
| C16:1n7 Palmitoleic (Omega-7) | 23.8 |
| C18:1n9 Oleic (Omega-9) | 12.7 |
| C18:2 Linoleic | 1.0 |
| C20:4n6 Arachidonic (Omega-6) | 1.6 |
| C20:5n3 Eicosapentaenoic (Omega-3) | 5.1 |
| Others | 1.4 |
| Total Fatty Acids | 84.4 |

Transesterification Step:

A traditional two stage transesterification method may be used with microalgae oil. During the first stage, the *Nannochloropsis* oil (1 kg) was transesterified in a 5 L, 3-neck round bottom flask using 8% w/w concentration. In the first transesterification stage, sulphuric acid was used as the acid catalyst and a 1:7 molar ratio of ethanol was used as the reacting solvent. The first stage reaction was performed for 3 hrs at 80° C. After 3 hrs, the second stage of transesterification was performed. In the second transesterification stage, the reaction mixture used 2.5% sodium ethoxide as the base catalyst and a 1:7 molar ratio of ethanol as the reacting solvent. The second stage reaction was performed for 3 hrs at 80° C. After completion of both reaction stages (6 hrs), the reaction mixture was cooled to ≤40° C. and neutralized with 1:1 v/v of water. The resulting mixture was extracted using hexane, forming a hexane layer on top comprising the target Omega-7 ethyl ester product which was separated and was concentrated using rotary evaporator resulting in ≥700 grams of the FAEE product (≥70% Yield).

Distillation Step:

With a microalgae oil mixture that contains less than 85% total fatty acids, as with the *Nannochloropsis* oil shown in Table 6, it is recommended that the first distillation step comprise a simple distillation under high vacuum in order to create a distillate with a total fatty acid content greater than 85%. The first step distillation may be performed with a short path distillation unit or simple distillation unit operated at a temperature at which all the fatty acids present will vaporize but below a temperature that causes thermal decomposition. With the *Nannochloropsis* FAEE product, the first step distillation was performed at a reboiler temperature of 275° C., a pressure of 2 mmHg, and a distillate temperature of 168° C.

After the simple or short path distillation step, a fractional distillation step may be performed on the purified FAEEs to fractionate C16:0 and C16:1 ethyl esters using conditions similar to conditions used for macadamia nut oil in Example 1. Variations from the parameters in Example 1 may be required due to the different molar fraction of C16:0 and C16:1 in microalgae oil as compared to the nut oil. With the *Nannochloropsis* FAEE product, the fractional distillation was performed at a reboiler temperature of 200° C., a pressure of 1 mmHg, and a distillate temperature of 144° C. The method of processing *Nannochloropsis* oil is shown in FIG. 3, and the resulting fatty acid concentrations of the resulting products from the molecular distillation are shown in Table 7.

TABLE 7

|  | Distillate (Omega 7) % | Residue (Omega 3) % |
|---|---|---|
| C14:0 | 7.19 |  |
| C14:1 | 0.41 |  |
| C15:0 | 0.56 |  |
| C16:0 | 41.31 | 8.71 |
| C16:1n7 (Omega-7) | 35.13 | 4.79 |
| C18:1n9 (Omega-9) | 5.93 | 22.78 |
| C18:2 | 1.02 | 3.49 |
| C18:3n6 | 0.19 | 0.59 |
| C20:1 |  | 0.33 |
| C20:3n6 |  | 0.92 |
| C20:4n6 (Omega-6) | 0.23 | 10.39 |
| C20:5n3 (Omega-3) | 0.66 | 33.37 |
| Total Fatty Acid Esters | 98.53 | 93.9 |

Figure 3:
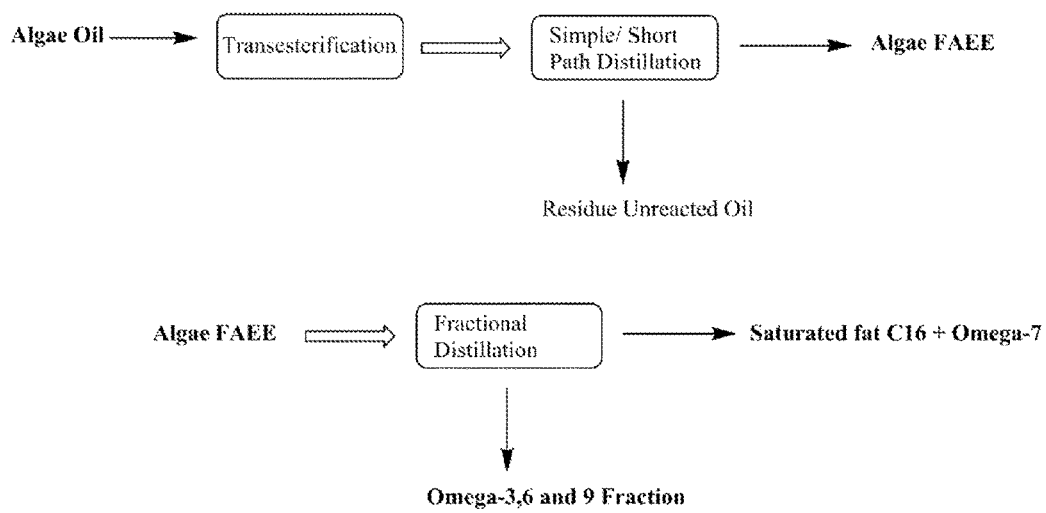
FIG. 3 illustrates non-limiting embodiments for isolating an Omega-7 product from natural microalgae oil.
Figure 4:
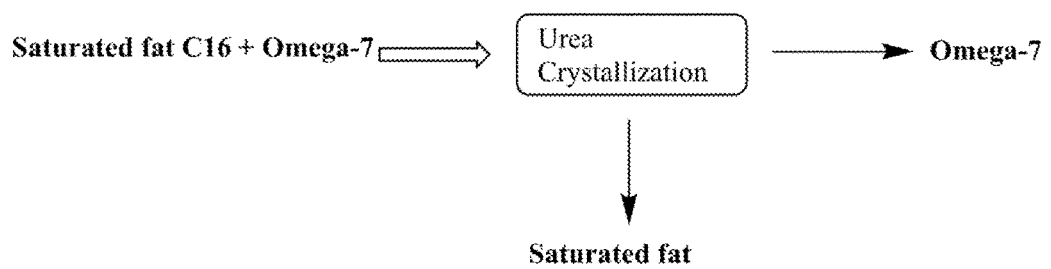
FIG. 4 illustrates a non-limiting embodiment for purifying an Omega-7 product isolated from natural microalgae oil.

The process shown in FIG. 3 produces two different fractions a first fraction comprising C18:1n9 (Omega-9), C20:4n6 (Omega-6), and C20:5n3 (Omega-3) ethyl esters and a second fraction comprising saturated C16 and C16:1 (Omega-7) ethyl esters, similar to resulting product in the macadamia nut oil FAEE distillation method of Example 1. The C16:0 and C16:1n7 (Omega-7) ethyl ester fraction resulting from the microalgae oil also has potential for commercial use in the cosmetics field due to the antimicrobial activity. The Omega-7 ethyl ester fraction may be further purified using a urea crystallization technique to achieve a high purity Omega-7 ethyl ester product as shown in FIG. 4 to produce a third fraction of C16:0 ethyl esters (saturated fats) and a fourth fraction comprising C16:1n7 (Omega-7) ethyl esters, thereby raising the concentration level of Omega-7 ethyl esters above the 35% shown in Table 7.

Figure 5:
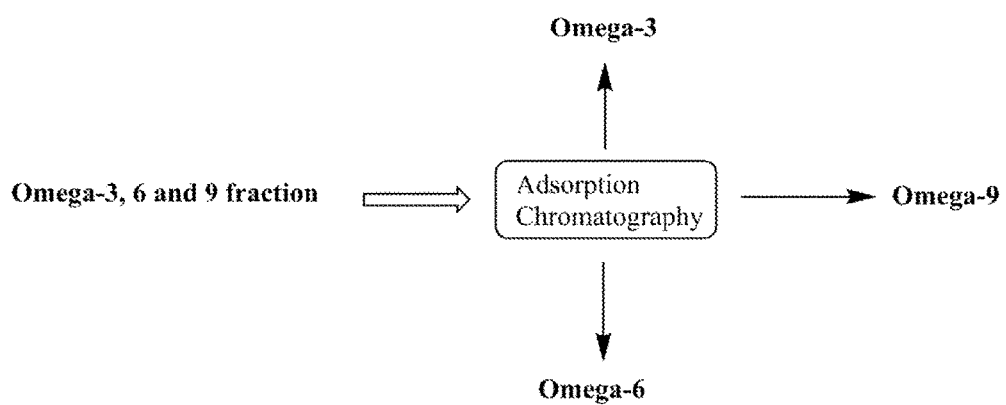
FIG. 5 illustrates a non-limiting embodiment for purifying an Omega-3, 6 or 9 product isolated from natural microalgae oil.

The method shown in FIG. 3 also produces an Omega-3, 6 & 9 ethyl ester rich first fraction. The fatty acids present in the Omega-3, 6, & 9 fraction have similar physical properties, allowing the use of adsorption chromatography (Silver-ion Chromatography) to separate these fatty acid ethyl esters and achieve higher purities. The adsorption chromatography selectively separates the fatty acid ethyl esters based on unsaturation and carbon chain length as shown in FIG. 5.

Figure 6:
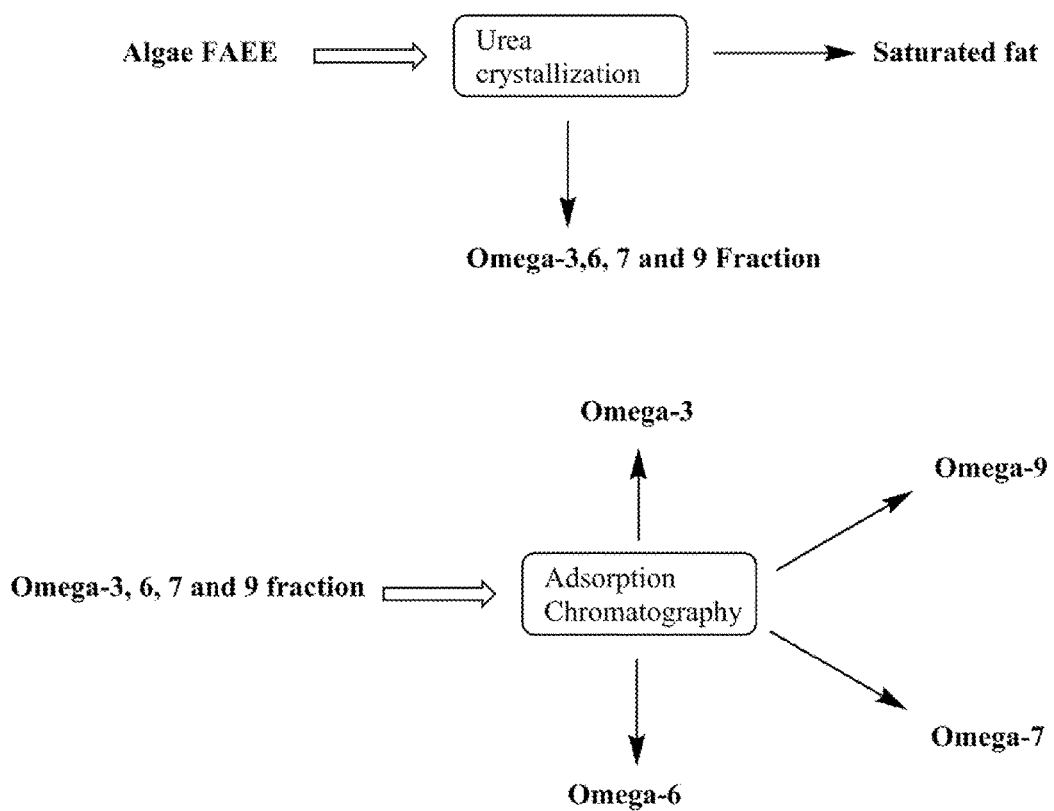
FIG. 6 illustrates a non-limiting embodiment for purifying an Omega-3, 6, 7 or 9 product isolated from natural microalgae oil.

Additionally, the microalgae FAEE produced with the method shown in FIG. 3 may be separated into a saturated fat fraction and a monounsaturated fatty acids (MUFA)+PUFA fractions using urea crystallization. A MUFA+PUFA fraction will contain Omega-3, 6, 7 & 9 fatty acid ethyl esters which have potential commercial value in nutraceutical applications and may be purified into individual components using adsorption chromatography as shown in FIG. 6.

Example 3

An experimental plan was formed to determine for isolating an Omega-7 ethyl esters product from natural fish oil. Natural fish oil from sources such as menhaden and anchovy are also known to be sources of nutritional fatty acids, including Omega-7 fatty acids. Natural menhaden oil was analyzed and found to contain the fatty acid profile shown in Table 8, and may be processed in a method similar to the methods described for macadamia nut oil in Example 1 to produce high purity fractions of Omega-3, 6, 7 & 9 ethyl esters.

TABLE 8

| Natural Menhaden Oil Composition | |
|---|---|
| Analyte | % (Average) |
| C14:0 | 8 |
| C16:0 | 18 |
| C16:1n7 (Omega-7) | 11 |
| C18:0 | 3.1 |
| C18:1n9 (Omega-9) | 8 |
| C20:5n3 (Omega-3) | 15 |
| C22:6n3 (Omega-3) | 7 |
| Total Fatty Acids | 70.1 |

Transesterification Step:

Fish oil (1 kg) may be transesterified in a 5 L, 3-neck round bottom flask using 2.5% w/w sodium ethoxide as the catalyst and a 1:10 molar ratio of ethanol as the reacting solvent. The reaction may be performed for 3 hrs at 80° C. After 3 hrs, the reaction mixture will be cooled to ≤40° C. and neutralized with 1:1 v/v of water. After neutralization the reaction mixture will separate into two layers comprising an ethyl ester layer on top and an aqueous layer on bottom. The ethyl ester layer will be separated and concentrated using a rotary evaporator resulting in ≥850 grams of the FAEE product (≥85% Yield).

Distillation Step:

A fish oil FAEE product with a composition of at least 20% w/w C16:1n7 ethyl esters may be concentrated to above 50% w/w C16:1n7 ethyl esters using a vacuum distillation apparatus in either a one-pass or two-pass system. The two-pass distillation system may be similar to the distillation system and method described in Example 2. In such a system, the reboiler temperature varies between 170° C. and 220° C., and the vacuum pressure is maintained at 0.3 to 5 mmHg. Using the single pass distillation system in conditions similar to Example 1 for the macadamia nut oil FAEE will result in a second fraction mixture of C16:0 and C16:1n7 ethyl esters. The resulting concentrated oil product may be successfully used in the cosmetics field, as the saturated fat along with Omega-7 also has antimicrobial activity.

Separation Step:

The second fraction distillate mixture (20 grams) resulting from the molecular distillation step may be treated with urea (2 times w/w) and ethanol (5 times w/v). The resulting reaction mixture will be refluxed at 80° C. for 2 hrs and then allowed to crystallize overnight (approximately 10-12 hrs). After overnight crystallization, the resulting crystals comprising saturated fats (C16:0) will be separated using a simple filtration system to form a third fraction of C16:0 ethyl esters. The fourth fraction liquid phase filtrate (fourth fraction) will be treated with water to remove the dissolved urea and the Omega-7 product will be extracted using hexane. The hexane layer will be concentrated using a rotary evaporator under vacuum to give the Omega-7 ethyl ester product as shown in FIG. 7.

Figure 7:
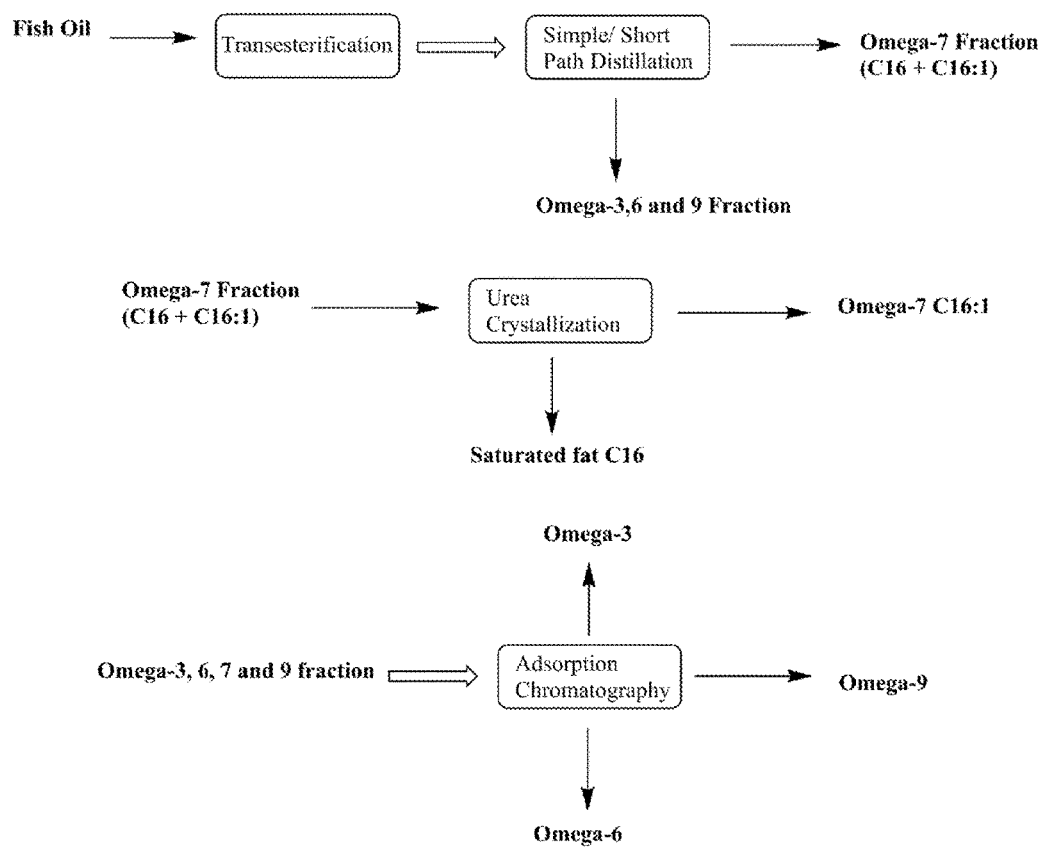
FIG. 7 illustrates non-limiting embodiments for isolating and purifying an Omega-3, 6, 7 or 9 product from natural fish oil.

Additionally, the Omega-3, 6, & 9 first fraction separated during the simple distillation step may be further purified using adsorption chromatography to further separate the Omega-3, Omega-6, and Omega-9 FAEE from each other as shown in FIG. 7.

Figure 8:
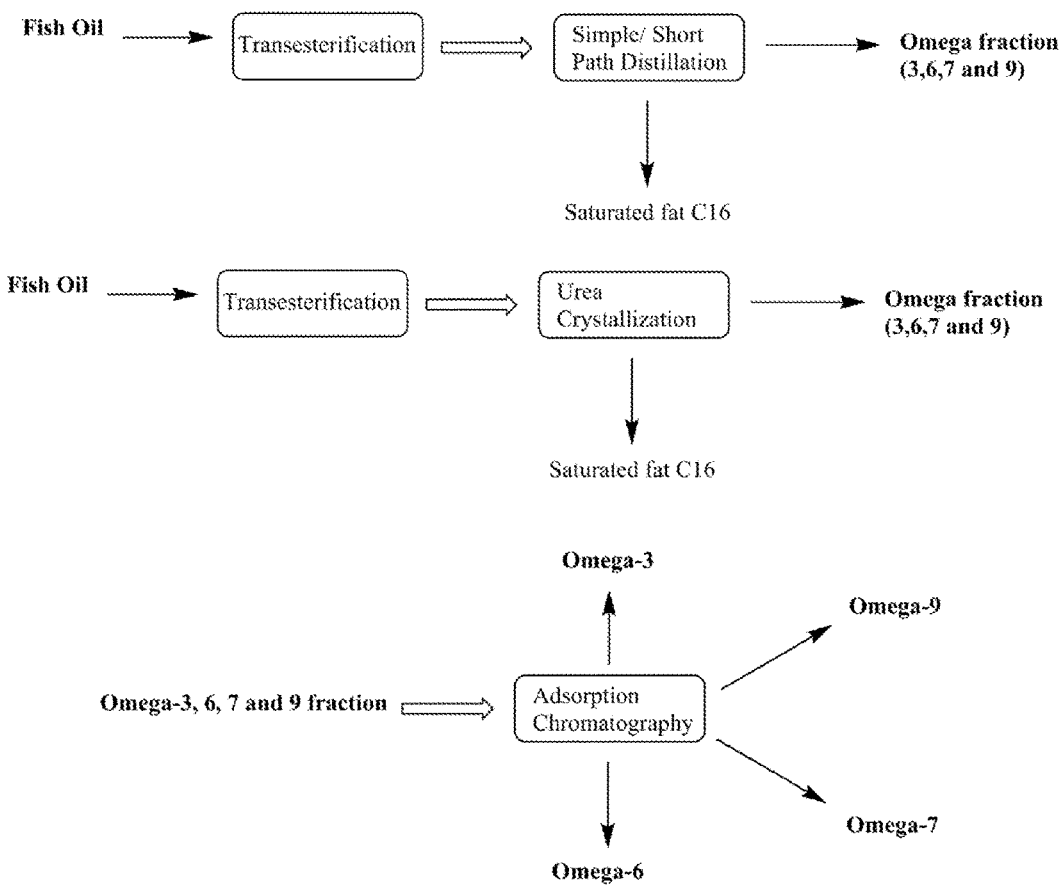
FIG. 8 illustrates non-limiting embodiments for isolating and purifying an Omega-3, 6, 7 or 9 product from natural fish oil.

A nutraceutical fraction (Omega-3) may also be produced from fish oil FAEE using either a molecular distillation method to remove fatty acids≤C16:0 or a urea complexation method to remove saturated fat. The Omega fraction separated from saturated fat may comprise Omega-3, 6, 7 & 9 FAEE, similar to the fraction separated from microalgae oil in Example 2. The Omega-3, 6, 7, & 9 fraction has potential value in a nutraceutical product as an Omega mixture. As shown in FIG. 8, the Omega fraction may also be further purified into individual fatty acids fractions using a technique such as adsorption chromatography to produce separate Omega-3, Omega-6, Omega-7, and Omega-9 fractions for use in nutraceuticals.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein. The citation and incorporation of patent documents herein is done for convenience only and does not reflect any view of the validity, patentability, and/or enforceability of such patent documents.

The use of the terms "a" and "an" and "the" and similar referents in the context of describing the invention are to be construed to cover both the singular and the plural, unless otherwise indicated herein or clearly contradicted by context.

Unless otherwise stated, all exact values provided herein are representative of corresponding approximate values (e.g., all exact exemplary values provided with respect to a particular factor or measurement can be considered to also provide a corresponding approximate measurement, modified by "about," where appropriate). All provided ranges of values are intended to include the end points of the ranges, as well as values between the end points.

The description herein of any aspect or embodiment of the invention using terms such as "comprising", "having," "including," or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

This invention includes all modifications and equivalents of the subject matter recited in the claims and/or aspects appended hereto as permitted by applicable law.

What is claimed is:

1. A method of producing high purity palmitoleic acid ethyl esters, comprising:
    a. Providing a natural oil;
    b. Transesterifying the natural oil with a catalyst and ethanol as a reacting solvent in a reaction comprising at least one stage to produce ethyl esters;
    c. Distilling the ethyl esters to produce a first fraction comprising C18:1n9, C20:4n6, and C20:5n3 ethyl esters, and a second fraction comprising C16:0 and C16:1n7 ethyl esters; and
    d. Separating the C16:0 and C16:1n7 ethyl esters of the second fraction to produce a third fraction of C16:0 ethyl esters and a fourth fraction comprising at least 50% w/w C16:1n7 ethyl esters.

2. The method of claim 1, wherein the natural oil consists of a natural oil comprising at least 5% C16:1n7 fatty acid.

3. The method of claim 2, wherein the natural oil comprises oil derived from at least one source selected from the group consisting of macadamia nut oil, menhaden oil, and anchovy oil.

4. The method of claim 1, wherein the catalyst of the transesterifying step comprises at least one catalyst selected from the group consisting of: NaOH, KOH, sodium ethoxide, HCl, $BF_3$, $H_3PO_4$, an organic sulfonic acid, sulphuric acid, a metal oxide, Mg—Al hydrolalcite, and an immobilized enzyme.

5. The method of claim 1, wherein the molar ratio of ethanol in the transesterifying step is in the range of 1:3 to 1:15.

6. The method of claim 5, wherein the molar ratio of ethanol in the transesterifying step is in the range of 1:6 to 1:8.

7. The method of claim 1, wherein the transesterifying step comprises two stages of transesterification reactions.

8. The method of claim 7, wherein the two stages of transesterification reactions use different catalysts.

9. The method of claim 1, wherein the transesterifying step has a yield in the range of 70-90%.

10. The method of claim 1, wherein the transesterifying step is performed at a temperature in the range of 75-85° C.

11. The method of claim 1, wherein the distillation step comprises at least one selected from the group consisting of one pass vacuum distillation, two pass vacuum distillation, fractional distillation, and simple molecular distillation.

12. The method of claim 1, wherein the separation step comprises at least one selected from the group consisting of urea complexation, crystallization, filtration, extraction, and adsorption chromatography.

13. The method of claim 1, wherein the fourth fraction comprises at least 80% w/w C16:1n7 ethyl esters.

14. The method of claim 3, wherein the second fraction derived from natural macadamia nut oil comprises less than 20% w/w C16:0 ethyl esters.

15. The method of claim 14, wherein the fourth fraction derived from natural macadamia nut oil further comprises less than 10% w/w C16:0 ethyl esters.

16. The method of claim 3, wherein the second fraction derived from natural macadamia nut oil comprises less than 1% w/w C18:1n9 ethyl esters.

17. The method of claim 16, wherein the fourth fraction derived from natural macadamia nut oil further comprises less than 5% w/w C18:1n9 ethyl esters.

18. The method of claim 3, wherein the second fraction derived from natural macadamia nut oil further comprises at least 70% w/w of C16:1n7 and C18:1n9 ethyl esters combined.

19. The method of claim 1, further comprising including the C16:1n7 ethyl esters in a product selected from the group consisting of a nutrition product, cosmetic product, and nutraceutical product.

20. The method of claim 11, wherein the distillation step is performed at a pressure in the range of 0.3-5 mm Hg and a temperature in the range of 140-280° C.

* * * * *